United States Patent [19]

Guerrero et al.

[11] Patent Number: 5,459,035
[45] Date of Patent: Oct. 17, 1995

[54] METHOD OF DETECTING THE TUMORS USING RING SHAPED PARTICLES AS A TUMOR MARKER

[75] Inventors: Robert R. Guerrero, Pasadena; Donald E. Rounds, Altadena, both of Calif.

[73] Assignee: AMDL, Inc., Pasadena, Calif.

[21] Appl. No.: 987,678

[22] Filed: Dec. 9, 1992

Related U.S. Application Data

[63] Continuation-in-part of Ser. No. 754,272, Aug. 20, 1991, abandoned, and Ser. No. 754,273, Aug. 30, 1991, abandoned, which is a continuation-in-part of Ser. No. 284,688, Dec. 5, 1988, abandoned, said Ser. No. 754,272, is a continuation-in-part of Ser. No. 552,409, Jul. 12, 1990, abandoned.

[51] Int. Cl.$^6$ .............................. C12Q 1/68; C12Q 1/00; C07K 15/00; C07H 17/00
[52] U.S. Cl. .............................. 435/6; 435/7.1; 435/7.23; 435/7.94; 436/503; 436/811; 436/813; 530/388.8; 530/388.24; 530/403; 530/828; 530/389.1; 536/23.1; 935/3
[58] Field of Search .............................. 435/7.1, 6, 7.23, 435/7.94; 530/388.21, 388.24, 403, 828, 388.8, 389.1; 436/503, 811, 813; 536/23.1; 935/3

[56] References Cited

U.S. PATENT DOCUMENTS

| | | | |
|---|---|---|---|
| 3,798,131 | 3/1974 | Rounds et al. | 195/103.5 |
| 5,059,521 | 10/1991 | Scherrer et al. | 435/7.1 |

OTHER PUBLICATIONS

Dang, *Cell Biology International Reports*, vol. 8, No. 4, 1984, pp. 323–327.
Leary, J. J. et al., *Rapid and sensitive colorimetric method for visualizing biotin–labeled DNA probes hybridized to DNA or RNA immobilized on nitrocellulose: bio–blots*, Proc. Natl. Acad. Sci. USA, 80, 4045–4049, Jul., 1983.
Forster, A. C. et al., *Non–radioactive hybridization probes prepared by the chemical labelling of DNA and RNA with a novel reagent, photobiotin*, Nucleic Acids Research, vol. 13 No. 3, 745–761, 1985.
Shelton, E. et al., *Cytoplasmic Particles and Aminoacyl Transferase I Activity*, The Journal of Cell Biology, vol. 45, 1–8, 1970.
Harris, J. R., *Comparative Studies on Cylindrin: Identity with Aminoacyl–tRNA Synthetase*, Micron Microscop. Acta 14, 193–205, 1983.
Domae, N. et al., *Novel Donut–Shaped "Miniparticles" in Nuclei of Human and Rat Cells*, Life Sciences 30:469–477, 1982.
Davis, F. M. et al., *Nucleolar antigen found in several human tumors but not in the y ynnontumor tissues studies*, Proc. Natl. Acad. Sci. USA, vol. 76, No. 2, pp. 892–896, Feb., 1979.
Kumatori, A. et al., *Abnormally high expression of proteasomes in human leukemic cells*, Proc. Natl. Acad. Sci. USA, vol. 87, pp. 7071–7075, Sep. 1990.
Narayan, K. S. et al., *Occurrence of Minute Ring–Shaped Nucleoprotein Particles in Culture Media Conditioned By Mammilian Cells*, in Vitro, vol. 12, No. 6, 436–441, 1976.
Narayan, K. S. et al., *Minute Ring–shaped Particles in Cultured Cells of Malignant Origin*, Nature New Biology vol. 243, 146–150, May 30, 1973.
Rounds, D. E., et al., *Prospects for a Personal Screening Method for Cervical Carcinoma*, Gynecologic Oncology 4, 125–132, 1976.

(List continued on next page.)

*Primary Examiner*—Margaret Parr
*Assistant Examiner*—Bradley L. Sisson
*Attorney, Agent, or Firm*—Christie, Parker & Hale

[57] ABSTRACT

A method is described for identifying and localizing tumors in a patient. The method comprises assaying extracellular fluids, isolated from a patient, for the presence of elevated levels of ring shaped particles (RSP). The assay employs binding labeled RSP specific binding agent to the RSP.

7 Claims, 4 Drawing Sheets

OTHER PUBLICATIONS

Rounds, D. E., et al., *Production of Ring–Shaped Particles by Normal and Metaplastic Tissue. I. Human Skin*, Journal of the National Cancer Institute, vol. 55, No. 1, 7–10, Jul., 1975.

Rounds, D. E., *A Growth–modifying Factor from Cell Lines of Human Maglinant Origin*, Cancer Research 30, 2847–2851, Dec., 1970.

Deutscher, M. P., *The Eucaryotic Aminoacyl–tRNA Synthetase Complex: Suggestions for its Structure and Function*, The Journal of Cell Biology, vol. 99, 373–377, Aug., 1984.

Reisfeld, A., et al., *Nonradioactive Hybridization Probes Prepared By the Reaction of Biotin Hydrazide with DNA[1]*, Biochemical and Biophysical Research Communications, vol. 142, No. 2, 519–526, Jan. 30, 1987.

Dang, C. V., *Identity of the Ubiquitous Eukaryotic Ring–Shaped Miniparticle*, Cell Biology International Reports, vol. 8, No. 4, 323–327, Apr., 1984.

Smulson, M., *Subribosomal Particles of HeLa Cells*, Experimental Cell Research 87, 253–258, 1974.

Kleinschmidt, J. A. et al., *The 22 S cylinder particles of Zenopus Laevis, I. Biochemical and electron microscopic characterization*, European Journal of Cell Biology 32, 143–156, 1983.

Harmon, F. R. et al., *Purification and Partial Characterization of Ring–shaped Miniparticles*, Cell Biology Intl. Reports, vol. 7, No. 5, 333–343, May, 1983.

Busch, H. et al., *Ultrastructural and Purification Studies on Human Tumor Nucleolar Antigens and Nucleolar Particles*, Cancer Investigation, 1(1), 25–40, 1983.

Busch, H. et al., *A Nucleolar Antigen Found in a Broad Range of Human Malignant Tumor Specimens*, Cancer Research 39, 3024–3030, Aug., 1979.

Wieczorek, A. J. et al., *Diagnostic and Prognostic Value of RNA–Proteolipid in Sera of Patients with Malignant Disorder following Therapy: First Clinical Evaluation of a Novel*, Tumor Marker, Cancer Research 47, 6407–6412, Dec. 1, 1987.

Wieczorek, A. J. et al, *Ein Gensondentest fur RNA–Proteolipid in Serumproben bei Neoplasie, Schweiz, Wschr. med.* 1989: 119; 1342–1343 (with attached translation).

Peters, J. M. et al., *An Abundant and ubiquitous homooligomeric ring–shaped ATPase particle related to the putative vesicle fusion proteins Sec 18p and NSF*, The EMBO Journal, vol. 9, No. 6, 1757–1767, Jun., 1990.

Busch, H. et al., *A Nucleolar Antigen Found in a Broad Range of Human Malignant Tumor Specimens[1]*, Cancer Research 39, vol. 39, 3024–3030, Aug. 1979.

Soel, J. H. et al., *Na+, K+–specific inhibition of protein and peptide hydrolyses by proteasomes from hyuman hepatoma tissues*, Febs Letters, vol. 247, No. 2, 197–200, Apr. 1989.

Tanaka, K. et al., *Proteasomes (Multicatalytic Proteinase Complexes) in Eukaryotic Cells*, Cell Structure and Function 15, 127–132 (1990).

METHOD OF DETECTING THE TUMORS USING RING SHAPED PARTICLES AS A TUMOR MARKER

CROSS-REFERENCE TO RELATED APPLICATIONS

This application is a continuation-in-part of U.S. application Ser. No. 07/754,272, filed Aug. 20, 1991, now abandoned which was a continuation-in-part of U.S. application Ser. No. 07/552,409, filed Jul. 12, 1990, now abandoned; and said application is a continuation-in-part of U.S. application Ser. No. 07/754,273, filed Aug. 30, 1991, now abandoned which was a continuation-in-part of U.S. application Ser. No. 07/284,688, filed Dec. 5, 1988, now abandoned.

FIELD OF THE INVENTION

The present invention relates to cancer detection and, more particularly, to a method for determining the presence of a tumor marker in extracellular fluids to reliably indicate the presence of cancer cells in a patient.

BACKGROUND OF THE INVENTION

Cancer is a large group of diseases characterized by uncontrolled cellular growth of, and invasion by, abnormal cells. If the spread is not controlled or checked, it results in death of the cancer patient. However, many cancers can be cured if detected early and treated promptly. The incidence of cancer is increasing.

Early detection of cancer greatly increases the potential for control. Detection of cancer in a localized or regional area, possibly with diagnosis early in the growth of the tumor, permits the use of more effective therapy, and improves the chance for recovery. Treatment by surgery, chemotherapy or radiation requires post-treatment monitoring to ensure that all vestiges of the malignant growth have been eliminated.

A number of tumor-associated metabolic products (markers) have been identified, some of which have been considered for use as tumor markers. Many of these tumor markers are uniquely associated with specific tumors. As a result, their presence can be used to reliably detect these tumors, making earlier, more reliable detection of the tumor possible. Some of the better known tumor markers are: carcinoembryonic antigen (CEA) for cancers of the colon, lung, stomach, and pancreas; alpha-fetoprotein (AFP) for testicular and liver cancers; and a tumor marker for breast cancer (CA15-3).

While some tumor markers have been identified, the number is very limited and directed at only a few forms of cancer. In addition, even if the number of individual tumor markers is expanded to include all forms of cancer, the routine diagnostic testing of patients would be very expensive and laborious since each form of cancer would require a separate test using each of the separate markers. The cost and time involved in such testing would preclude general screening of the population, therefore a form of testing is needed that would be most effective for the early diagnosis and treatment of malignancies before they become clinically manifest.

It is desirable that a test system is developed which is cost effective and which will detect any form of cancer in a single test. It is also desirable that such a test is not affected by background reactions which result from the source of the material tested and that the test is sensitive enough to detect the tumor marker at very early stages in the development of the tumor. It is also desirable that the test is simple to perform. It is also preferable that the test be performed on extracellular fluid samples which can be easily obtained in a doctor's office, or by the patient themselves, without the need for biopsy procedures.

SUMMARY OF THE INVENTION

A method is described for identifying tumors in a patient. The method comprises assaying extracellular fluids, isolated from a patient, for the presence of elevated levels of ring shaped particles (RSP). The assay employs binding labeled RSP specific binding agent to the RSP.

In one embodiment of the present invention the assay employs a "sandwich type" of assay in which RSP specific binding agent is immobilized on a surface. The immobilized RSP specific binding agent is then placed in contact with a sample of extracellular fluid, isolated from a patient, to form a captured complex. The captured complex is then contacted with a labeled specific binding agent to form a labeled captured complex. The amount of RSP in the captured complex is then quantitated.

In another embodiment of the present invention the assay employs a "dip-stick" type assay in which RSP, in an extracellular fluid sample, are bound to a surface. The bound RSP are then contacted with a labeled RSP specific binding agent to form a labeled captured complex. The amount of RSP in the captured complex is then quantitated.

In another embodiment of the present invention the assay employs a "competition type" assay. In one embodiment of the competition assay RSP are immobilized on a surface. RSP, in an extracellular fluid sample, are bound to labeled RSP specific binding agent, in solution. Any labeled RSP specific binding agent remaining in solution, unbound to RSP, is then bound to the immobilized RSP. In another embodiment of the competition assay RSP specific binding agent is immobilized on a surface. RSP, in an extracellular fluid sample are mixed with labeled RSP specific binding agent, in solution. The labeled RSP specific binding agent/RSP mixture is then contacted with the immobilized RSP specific binding agent. Labeled specific binding agent, which remains unbound to RSP, is available to bind to the immobilized RSP. In both competition assays the amount of label bound to the immobilizing surface is inversely proportional to the concentration of RSP in the extracellular fluid sample.

The present invention is also directed at methods for identifying the location of a tumor in a patient and treating such tumors. The method for localization of a tumor comprises injecting a labeled RSP specific binding agent into a patient, wherein the label can be detected by scanning techniques.

The specific binding agent of the present invention is selected from the group consisting essentially of tRNA and anti-RSP antibodies and the labeled specific binding agent is selected from the group consisting essentially of labeled tRNA, labeled anti-RSP antibodies and labeled peptides.

BRIEF DESCRIPTION OF THE DRAWINGS

These and other features and advantages of the present invention will become better understood with reference to the following description, appended claims, and accompanying drawings, wherein:

DETAILED DESCRIPTION

Figure 1:
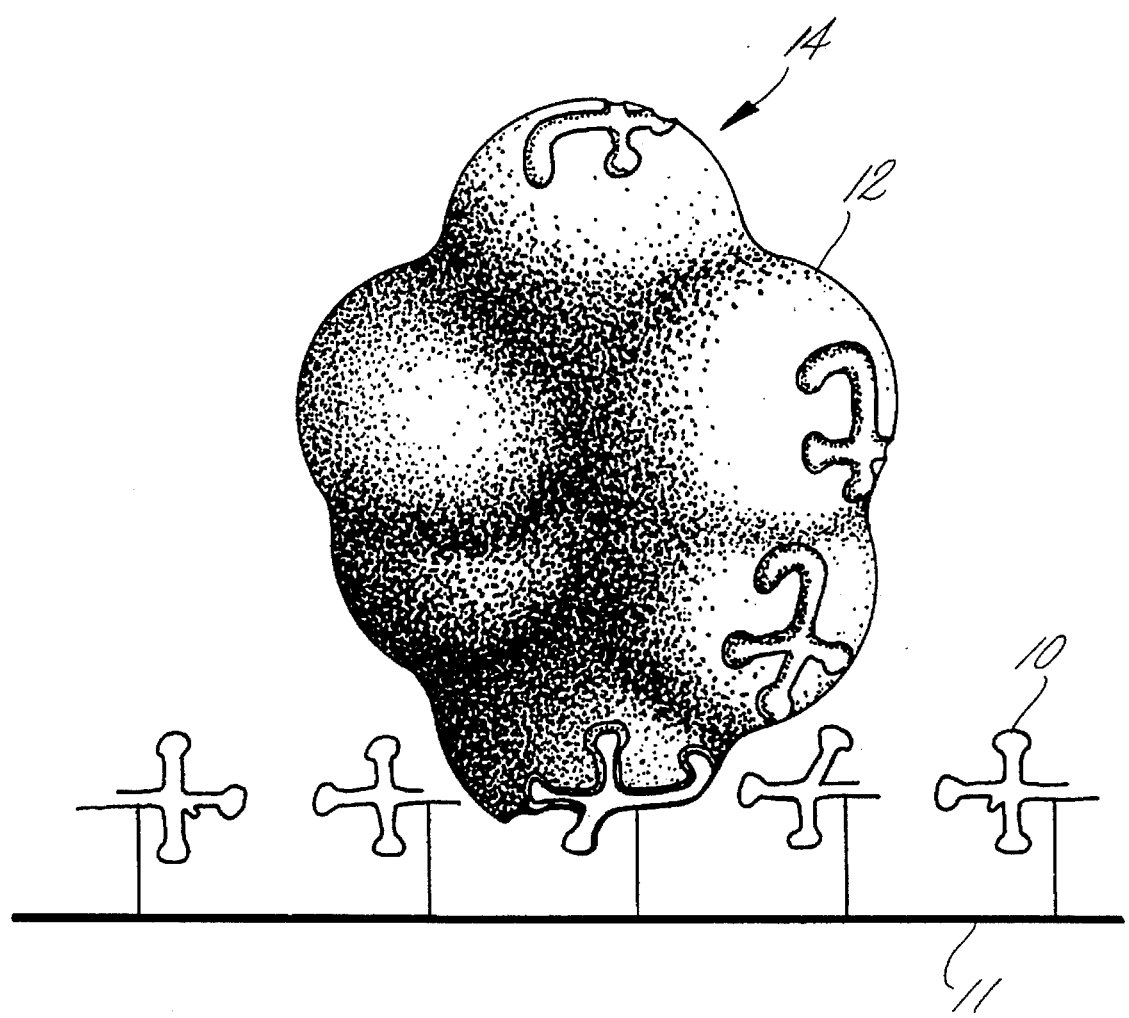
FIG. 1 illustrates, in diagrammatic fashion, a ring shaped particle (RSP) bound to a surface via RSP specific binding agent pretreated surfaces.

The present invention relates to a tumor marker which has been identified to be a universal tumor marker. This tumor marker is an intracellular complex known as ring shaped particles (RSP). The invention further relates to the discovery that the RSP are present in all cells, normal or cancer, and are secreted into extracellular fluids. Specific purification and assay methods have been developed, which are described in detail below, for isolating and assaying the RSP which eliminate interference from normal extracellular fluid components. The purification and assay methods are amenable to general, diagnostic screening for cancer.

The RSP tumor marker was first described in about 1970 by Rounds as a growth modifying factor found in conditioned tissue culture medium. In vitro studies indicated that the factor, at low concentrations, stimulated cell division. At intermediate concentrations the factor arrested cell division and, at high concentration, caused cell death.

The factor has been found to consist of particles with a ring configuration, comprising about 6–7 subunits of about 10 to 12 nanometers (nm) in diameter. The particles contain about 3–5 micrograms (μg) of DNA and about 8–15 μg of RNA for each 100 μg of protein assayed.

Research has indicated that intracellular levels of RSP are indicative of a tumor. A nucleolar antigen extracted from the nucleoli of a variety of cancer cells was observed to consist of "mini-particles" having an outside diameter of 11.3 nm and an inner diameter of 2.9 nm, containing 8 subunits and having the overall morphologic appearance of the RSP. This antigen was found to be present in carcinomas of the bladder, brain, colon, esophagus, liver, lung, prostate, skin, stomach and thyroid, 3 kinds of sarcomas, 4 kinds of lymphomas and 6 cultured cell lines of malignant tissue origin. The antigen was found to be absent in 17 normal tissue types, 4 benign tumors, 7 types of inflammatory diseases and 2 cultured cell lines of normal origin. However, the use of intracellular components is not effective for the routine testing of patients or the general population since such testing would have to rely on biopsy samples from the cancerous tissue.

Early research resulted in the development of a fluorescence assay system for detecting the DNA component in the RSP (U.S. Pat. No. 3,798,131 to Rounds et al.). The assay method relied on the binding of ethidium bromide to the DNA component of RSP. The results of the assay were determined by a change in the fluorescence of the sample. This assay technique was reportedly successful when used with tissue extracts, conditioned tissue culture medium and vaginal irrigation fluids, for screening women for cervical cancer. The results suggested that RSP may be secreted into extracellular fluids. However, the test was found to be unreliable in other test situations such as screening serum samples. In these cases the serum was found to contain many "normal components" which could interact with the ethidium bromide to give false positive, and therefore unreliable, results.

While there is a growing body of information which indicates that RSP are an intracellular marker for tumors, earlier results reporting that RSP were secreted by cancer cells have been generally concluded to be artifactual, due to the high background reading observed with the ethidium bromide assay with normal extracellular fluid components. This conclusion, that the RSP are intracellular and not secreted, has generally led to an abandonment of RSP assays as a screening method for cancer detection, since biopsy samples of the cancer tissue would be required to perform the test.

Following this erroneous logic, it was believed by others that, even if RSP were secreted into extracellular fluids, the background reaction of the ethidium bromide assay with normal extracellular fluid components would require extensive purification of the RSP before assaying, making such an assay impractical for routine testing. As a result of the unreliability of the assay technique and the accumulated literature which suggested that the basis for the assay procedure was not valid, since RSP were not secreted into extracellular fluids, no developments in the use of RSP as a cancer test method have been reported in the 18 years since the issuance of the Rounds et al. patent.

The present invention is based on the confirmation that RSP are in fact secreted into extracellular fluids. An assay method for determining the presence of such RSP tumor markers involves isolating or capturing RSP molecules from an extracellular fluid sample with a specific binding agent also referred to as RSP specific binding agent. The specific binding agent recognizes the RSP molecule but not other components of the extracellular fluid. The presence of the RSP molecule in the "captured" complex is then assayed by the use of a labeled specific binding agent. This method of "purifying" the RSP is effective in isolating the RSP from extracellular fluid components which may interfere with the assay procedures involved.

Figure 2:
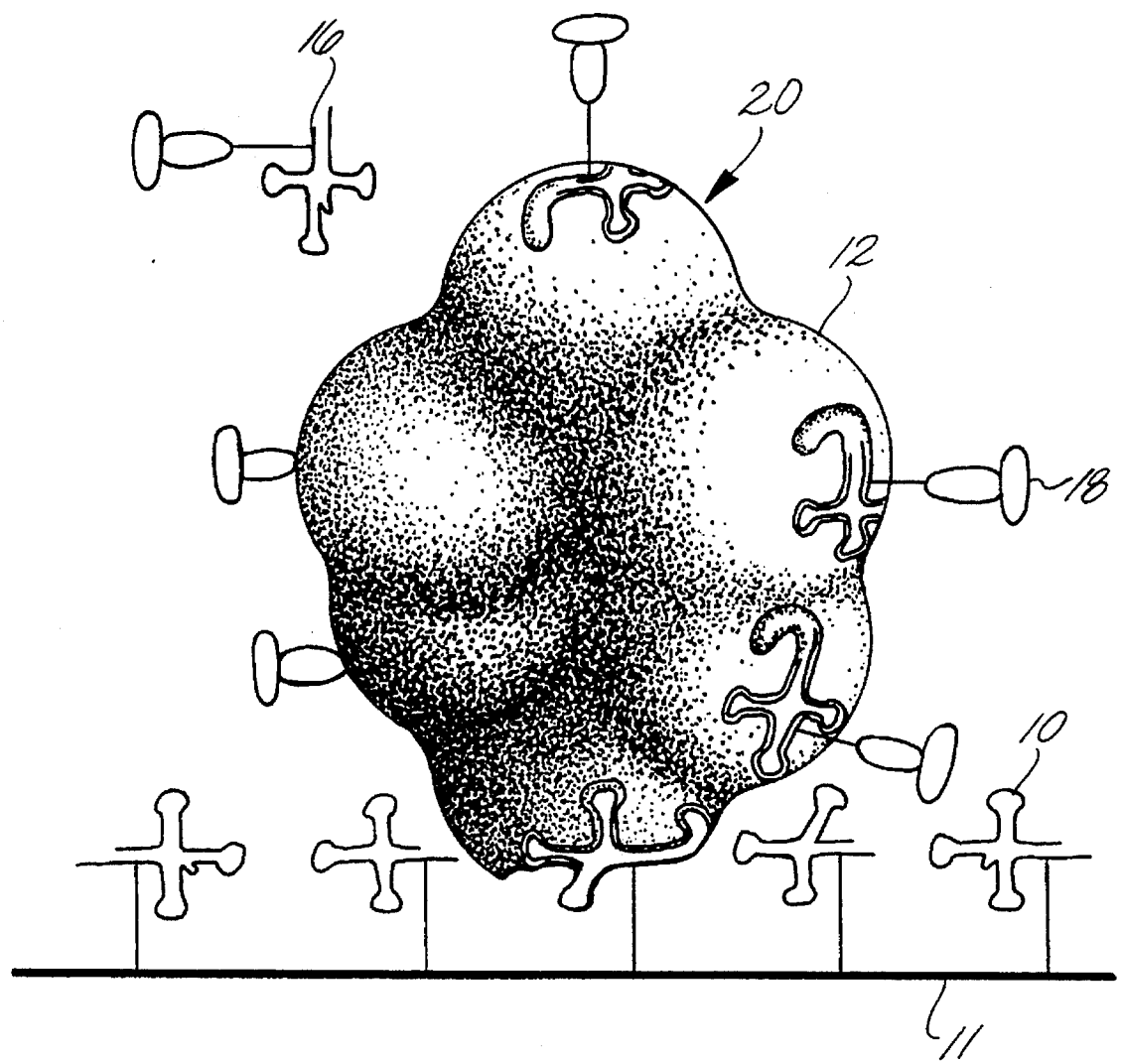
FIG. 2 illustrates, in diagrammatic fashion, the RSP of FIG. 1 following reaction with labeled RSP specific binding agent at the RSP's binding sites.

The methods of assaying RSP particles, as described below, have been found to be very sensitive and have established that RSP are not only secreted from tumor cells but also, to a much lesser degree, by normal aging cells. Therefore, it is necessary in performing the tests described below, to include controls to estimate "normal" RSP levels. Assay results which give values above this normal level are indicative of the presence of a tumor. Briefly, the method of one embodiment of the present invention is to obtain a sample of an extracellular fluid from a patient and place it in contact with a specific binding agent 10 immobilized on a surface 11 as illustrated in FIG. 1. Due to the affinity between the specific binding agent and the RSP 12, any RSP in the sample becomes attached to the specific binding agent to form a captured complex 14. The captured complex is rinsed several times, with a suitable buffer, to wash all of the extracellular fluid sample from the captured complex. A quantity of labeled specific binding agent 16, as illustrated in FIG. 2, where the specific binding agent illustrated is tRNA, is added to the captured complex. The labeled specific binding agent binds to the RSP, as shown by 18, in the captured complex to form labeled captured complex 20. The labeled captured complex is rinsed, with a suitable buffer, to wash away unbound labeled specific binding agent. At this juncture, it remains only to provide a visual indication of the quantity of RSP in the captured complex. This and other embodiments of the present invention are described in detail below.

I. Detection of RSP

The detection of RSP relies on the ability of a specific binding agent to bind selectively with RSP.

A. Specific Binding Agents

A specific binding agent is a compound or molecule which binds to an RSP in a specific, rather than a nonspecific manner. RSP bind agents such as DNA, RNA, tRNA and anti-RSP antibodies. Each of these agents would be suitable for use as a specific binding agent, as could other molecules which specifically interact with RSP, such as proteins or peptides which are recognized by a proteinase activity endogenous to the RSP. In preferred embodiments of the present invention the specific binding agents are tRNA and anti-RSP antibodies. These agents and their use are discussed in detail below.

1. tRNA as an RSP Specific Binding Agent

In one embodiment of the present invention a specific binding agent comprises transfer ribonucleic acid (tRNA). The utility of the tRNA as a specific binding agent for the RSP molecule relies on the discovery that the RSP comprise aminoacyl tRNA synthetase (aa-tRNA synthetase) activity. Thus, the binding agent is a substrate for the aa-tRNA synthetase. The binding of a substrate to an enzyme is very specific and eliminates many nonspecific reactions with other components which may be found in an extracellular fluid. This interaction can be used to capture and assay RSP particles. The reaction catalyzed by an aa-tRNA synthetase is as follows:

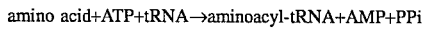

amino acid+ATP+tRNA→aminoacyl-tRNA+AMP+PPi

In the absence of ATP in the reaction mixture, tRNA is bound to the aa-tRNA synthetase, and remains bound, trapped in the dinucleotide fold at the active site of the aa-tRNA synthetase. The reaction is unable to proceed to completion without ATP. Therefore, the absence of ATP in the reaction mixture is useful in the formation of a relatively stable tRNA-aa-tRNA synthetase intermediate. In addition, since the binding of ATP to the aa-tRNA synthetase is usually via a $Mg^{2+}$ "salt bridge," the absence of $Mg^{2+}$ from the reaction mixture prevents the binding of ATP to the aa-tRNA synthetase and also results in the formation of the relatively stable tRNA-aa-tRNA synthetase intermediate. $Mg^{2+}$ can be effectively eliminated from a reaction mixture by the addition of a chelating agent such as ethylenediaminetetraacetate (EDTA).

2. Antibodies as a Specific Binding Agent

In another embodiment of the present invention the specific binding agent is an anti-RSP antibody. The interaction of an antibody with an antigen is a specific reaction, well known in the art. Such a specific interaction can be applied to the capture and assay of RSP. Polyclonal or monoclonal antibodies are suitable for use in the present invention. The method of preparation of both polyclonal and monoclonal antibodies is well known in the art.

Currently, affinity purified polyclonal antibodies are preferred, since the RSP is a "polymorphic molecule" which may contain different subcomponents at different times or when isolated by different methods. Therefore, if a single monoclonal antibody is used, the antigenic determinant recognized by that particular antibody could be missing in some preparations of RSP. Thus, the use of a single monoclonal antibody could lead to false negative results in some cases. To counteract this possibility, it is preferable that polyclonal antibodies, which recognizes a broad array of antigenic determinants on the RSP, are used. Alternatively, it is also expected that mixtures of monoclonal antibody, which recognize different antigenic determinants, would also be suitable for use in the present invention.

Where mixtures of monoclonal antibodies are to be used, the different cell lines producing the monoclonal antibodies (hybridomas), could be easily identified from a single fusion experiment. Screening of the hybridomas could be conducted, in accordance with the practice of the present invention, by immobilizing the antigen using either tRNA or polyclonal anti-RSP antibodies to a surface. The captured complexes are then reacted with monoclonal antibodies produced by the hybridomas. The bound monoclonal antibodies are detected with labeled anti-mouse antibodies.

Alternatively, the antibodies from the hybridoma cultures could be used as the specific binding agent and labeled tRNA or polyclonal antibodies could be used as the assay specific binding agent. In either case the assays would be performed using samples known to contain RSP. The details of the methodology required to perform these assays are described in detail below.

B. Detection of RSP Using "Sandwich" Type Assays

In a "sandwich" type assay a binding agent (BA) is immobilized to a surface (S) and an analyte (A) is bound to the binding agent. The presence of the analyte is then detected by binding a labeled binding agent (LBA) to the analyte. The resultant complex can be represented as follows:

S—BA—A—LBA

The analyte is "sandwiched" between two binding agents. In the present invention the sandwich assay is performed as described in detail below.

1. Immobilization of Specific Binding Agents

The first step in performing a sandwich type assay is to immobilize a specific binding agent by binding it to a surface.

a. Immobilization of tRNA

In the practice of the present invention tRNA is bound to an immobile surface such as, a well of a microtiter plate, glass slides, a bead surface (such as magnetic beads, colloidal gold, latex beads, acrylic beads, chromatography medium beads), nitrocellulose membranes or to other similar immobilizing surfaces. tRNA suitable for use in the present invention can be any tRNA fractions such as that supplied by Sigma Chemical Co., St Louis Mo. (Cat. No. R 0128). The methods of immobilizing tRNA molecules to the above-described surfaces are well known in the art.

In a preferred embodiment of the present invention tRNA is immobilized on streptavidin coated polystyrene plates by a biotin/avidin linkage. The polystyrene plates are coated with streptavidin by contacting the wells of the plates with about 100 µl of about 20 µg/ml solution of streptavidin in a buffer such as 137 mM NaCl, 1.6 mM KCl, 8.1 mM $Na_2HPO_4$, $KH_2PO_4$, adjusted to a pH of 7.2 (PBS). The plates are then incubated at about 37° C. for at least 2 hrs. Any unreacted sites are blocked by incubating the wells for about two hours at 37° C. with about 300 microliters (µl) of 3% w/v bovine serum albumin (BSA) or other suitable blocking material.

Biotinylated tRNA is then bound to the streptavidin coated plates. tRNA is linked to biotin hydrazide by replacement of cytidine in the tRNA by hydrazide when catalyzed by bisulfite at pH 4.5. Briefly, a mixture of about 50 µg/ml of tRNA, about 10 mg/ml biotin hydrazide, about 1M bisulfate, about 1M acetate buffer, pH 4.5, in a final volume of about 1ml, is incubated at 37° C. for about 24 hrs. After the incubation the solution is dialyzed against water at 4° C. for 24 hrs. The dialyzed solution is then dried under vacuum and resuspended in 10 mM Tris-HCl, pH 7.6, 0.1 mM EDTA.

The biotinylated tRNA is then combined with the streptavidin coated wells. When combined the streptavidin, which has a high affinity for biotin, binds to the biotin in a noncovalent reaction that is essentially irreversible. After the combination of the streptavidin and biotin the wells are washed with PBS, adjusted to a pH of 7.2, or other suitable buffer or wash solution, to remove any unbound biotinylated tRNA.

b. Immobilization of Antibodies

In the practice of the present invention an anti-RSP antibody is noncovalently bound to an immobile surface such as the wells of a polystyrene or polyvinylchloride microtiter plate, polyvinylchloride sheets, glass slides, a bead surface (such as magnetic beads, colloidal gold, polystyrene beads, latex beads, acrylic beads, chromatography medium beads), nitrocellulose membrane or to other similar immobilizing surfaces. Alternatively, covalent binding to diazotized activated paper or beads through free amino groups is also suitable for practice of the present invention. In some cases anti-RSP antibodies may be immobilized by binding them to an immobilized antibody-binding protein. Such proteins include Protein A, from *Staphylococcus aureus*, or Protein G, from Streptococcus sp. and are well known in the art. Such immobilized proteins, bound to chromatography media, are commercially available from suppliers such as Calbiochem of San Diego, Calif. and Pharmacia of Uppsala, Sweden.

When an antibody is contacted with the antibody binding protein it becomes bound, via the Fc portion of the antibody molecule. Since antibodies react with antigen through the Fab portion of the antibody molecule, binding to the antibody-binding protein does not interfere with the antibodies ability to bind antigen. Therefore, the antibody is capable of binding to both the antibody binding protein and antigen at the same time.

In a preferred embodiment anti-RSP antibodies are immobilized on polystyrene plates by noncovalent binding by contacting the wells of the plates with about 100 μl of about 20 μg/ml solution of affinity purified anti-RSP antibodies, in PBS, adjusted to a pH of about 7.2, and incubating the wells at about 37° C. for about 1 hr. Any unreacted sites are blocked by incubating the wells for about 2 hours at 37° C. with about 300 microliters (μl) of 3% w/v bovine serum albumin (BSA) or other suitable blocking material.

2. Formation of a Captured RSP Complex

In the practice of the present invention an immobilized binding agent is contacted with a sample suspected of containing RSP. The samples suitable for use in the present invention are extracellular fluids such as serum, sputum, urine, irrigation fluids and other such fluids which are likely to contain RSP secreted from a tumor bearing tissue. In addition, extracts from tissue biopsies or other tissue samples could also be used.

a. Preparation of RSP Captured Particles in Microtiter Wells

Microtiter wells, are coated with the specific binding agent, either tRNA or anti-RSP antibodies, and blocked with BSA or other suitable blocking material. The blocked microtiter wells are then contracted with about 100 μl of sample, suspected of containing RSP. The sample is allowed to remain in contact with the immobilized binding agent on the surface of the wells for about 120 min. at about 37° C., with gentle rocking. During this time any RSP in the sample is complexed with the specific binding agent to form an RSP captured complex. Unbound material is then washed from the complex with Dulbecco's phosphate buffered saline, adjusted to a pH of 7.2 (DPBS; 56 mM NaCl, 2.6 mM KCl, 8 mM $Na_2HPO_4$, 0.7 mM $CaCl_2$, 1 mM $MgCl_2$ and 7.7 mM $NaN_3$) or other suitable buffer.

b. Preparation of RSP Captured Particles on Beads

Where a bead has been coated with the specific binding agent and blocked with 3% w/v BSA, or other suitable blocking material, as described above, RSP captured complexes may be formed by contacting about 65 μg of coated beads with sample, suspected of containing RSP, which has been diluted about 1:150 in DPBS, adjusted to a pH of 7.2. This can be performed by mixing the sample with the coated beads. The sample-bead mixture is incubated for about 20 min. at about 37° C. to form a captured RSP complex. The captured complex is then collected by filtration through a glass fiber filter. Alternatively, the captured complex may be collected by centrifugation at 1,500×g for 5 min. The collected material is washed by resuspending it in DPBS, adjusted to a pH of 7.2, or other suitable buffer. The captured complex is then collected by filtration or centrifugation, as described above.

If magnetic beads are used the resultant captured complex is collected by placing the mixture in close proximity with a magnet, rather than by filtration or centrifugation.

In another embodiment of the present invention, beads coated with specific binding agent, are packed into a column and the sample, suspected of containing RSP, is passed through the column. As the sample moves through the column any RSP present in the sample is bound to the specific binding agent to form a captured complex. Unbound material is washed from the bead material by passing PBS, adjusted to a pH of 7.2, or other suitable buffer, through the bead material.

c. Preparation of RSP Captured Particles on Nitrocellulose Membranes

Where a nitrocellulose membrane has been coated with the specific binding agent any unbound sites on the nitrocellulose are blocked by contacting the coated nitrocellulose with 3% v/v fetal bovine serum (FBS) or other suitable blocking material. The blocked nitrocellulose is then washed with PBS, adjusted to a pH of 7.2, or other suitable buffer.

The blocked, washed nitrocellulose is contacted with about 50 μl of sample, suspected of containing RSP, for each $mm^2$ of nitrocellulose. The sample is allowed to remain in contact with the immobilized binding agent on the surface of the nitrocellulose for about 15 min., at about 37° C., during which time any RSP in the sample is complexed with the specific binding agent to form an RSP captured complex. Unbound material is then washed from the captured complex with PBS, adjusted to a pH of 7.2, or other suitable buffer.

3. Labeling of Specific Binding Agents

Once a captured complex is formed the next step is to assay the captured complex to determine if there is any RSP present on the immobilized surface. Assaying is conveniently performed by binding a labeled specific agent to RSP in the captured complex.

a. Labeling of tRNA

Labeling of tRNA may be performed by linking the tRNA to an agent such as biotin hydrazide which permits easy linkage of tRNA with: an enzyme such as glucose oxidase, alkaline phosphatase, peroxidase or the like, conjugated to streptavidin or avidin (such avidin-enzyme conjugates are commercially available and are sold by Sigma Chemical Co., Cat. Nos. A 7294 and A 3151, for example); a fluorescent marker such as fluorescein, rhodamine, Texas Red, ethidium bromide, acridine dyes and the like; radioactive labels; or with other labels which are well known in the art.

In a preferred embodiment the tRNA is linked to biotin hydrazide by replacement of cytidine in the tRNA by hydrazide when catalyzed by bisulfite at pH 4.5 as described above.

b. Labeling of Antibodies

The anti-RSP antibodies can be labeled radioactively, by conjugation to enzymes, with bio- and chemi-luminescent labeling systems, with biotin, or with colored beads or other such labels which are well known in the art.

In a preferred embodiment the anti-RSP antibodies are labeled with alkaline phosphate by glutaraldehyde conjunction. About 1 mg of antibody is mixed with about 0.5 of mg alkaline phosphatase suspension, such as that purchased from Sigma Chemical Co., as a 40% suspension in a 65% saturated ammonium sulfate. The mixture is centrifuged at about 4,000×g in a microcentrifuge for about 6 min. The pellet is resuspended in about 1 ml of 0.1M sodium phosphate buffer, pH 6.8 and dialyzed against 0.1M sodium phosphate buffer, pH 6.8, at 4° C. over a period of at least 24 hrs.

About 2.0 µl of glutaraldehyde is added to the dialysate and the mixture is stirred slowly for about 5 min. and then incubated at room temperature for about 17 hrs. After the incubation, about 1 ml of 0.1M ethanolamine, pH 7.0, is added and the mixture is incubated for about 2 hrs. At the end of this incubation the mixture is dialyzed overnight at 4° C. against 0.1M sodium phosphate buffer, pH 6.8.

The dialysate is centrifuged in a microcentrifuge at about 4,000×g for about 30 min. The resultant pellet was resuspended in about 4 ml of 4 mM $ZnCl_2$ and 4 mM $MgCl_2$ and about 4 ml of a 100% v/v glycerol is added to give a final concentration of 2 mM $ZnCl_2$ and 2 mM $MgCl_2$ in 50% v/v glycerol and the pH of the solution is adjusted to 6.0 and sodium azide is added to a concentration of 0.025% w/v.

The reagents are adapted for use in a commercially available testing device, the IMX, manufactured by Abbott Laboratories. The captured antibody-bead reagent is used at a 1:20 dilution and the labeled antibody at a 1:250 dilution in 50 mM Tris, pH 7.5, 20% v/v glycerol, 0.02% w/v sodium azide and 1 mM $ZnCl_2$.

c. Labeling of Peptides

Peptides or proteins can be used to assay for a proteinase, endogenous to the RSP. The proteinase has a specificity for the peptide sequence:

-Glu-Phe-Leu-Phe

The peptide can be linked to a compound such as methoxynaphthylamine (MNA) or 6-aminoquinoline (AQA):

-Glu-Phe-Leu-Phe-MNA (AQA)

Upon digestion with the RSP proteinase, MNA or AQA is liberated from the peptide. The free MNA or AQA is fluorescent, while the MNA or AQA attached to the peptide is nonflurorescent. In a simplified assay procedure Phe-AQA is used as a substrate. Such substrates can be prepared under contract by companies such as Molecular Probes of Eugene, OR.

In such reactions the substrate is incubated with captured complex, or alternatively, a sample suspected of containing RSP, for about 1 hr. at 37° C. After the incubation, the free fluorescent agent is detected in a fluorimeter such as a FLUOROSKAN II (supplied by Labsystems Instruments, Raleigh, N.C.). The sample is exposed to excitation light at a wavelength of 366 nm and the fluorescent light is measured at 560 nm. The amount of fluorescence observed is directly proportional to the amount of RSP present in the sample tested.

4. Binding of the Labeled Specific Binding Agent to Captured RSP Complex

To determine if any RSP is contained in the captured complex, the labeled specific binding agent is incubated with the captured complex. In a typical reaction, about 50 µg of 5 mg/ml (0.25 µg) labeled tRNA or about 100 µl of 0.03 µg/ml (0.003 µg) of labeled anti-RSP antibody, in DPBS, adjusted to a pH of 7.2, is added to the captured complex and the mixture is incubated at about 37° C. for about 60 min. with gentle rocking. At the end of the incubation the labeled captured complexes are washed with DPBS, adjusted to a pH of 7.2, or other suitable buffer, to remove any unbound labeled specific binding agent.

It should be noted that, captured complexes which use tRNA as the capturing agent, can be assayed by binding either labeled tRNA, labeled anti-RSP antibodies, labeled peptides or other labeled agents which recognize RSP. Similarly, captured complexes which use anti-RSP antibodies as the capturing agent can be assayed by binding either labeled tRNA, labeled anti-RSP antibodies, labeled peptides or other labeled agents which recognize RSP.

5. Assaying for the Labeled Specific Binding Agent Bound to the Captured RSP Complex The method of assaying for the labeled specific binding agent depends on the label used. Where the specific binding agent has been labeled with an enzyme, substrates for the enzyme are added to the labeled captured complex. Preferably the substrates chosen are ones which will give a colored product so that the development of color gives a simple and direct means of quantitating the results of the assay. The development of color, above background, indicates the presence of RSP in the extracellular fluid sample.

When the label is a fluorescent marker, the assay comprises exposing the labeled captured complex to an excitation light source. The presence of fluorescence indicates the presence of RSP in the extracellular fluid sample.

When the label is a chemiluminescent marker, the presence of chemiluminescence indicates the presence of RSP in the extracellular fluid sample.

When the label is a radioactive label the assay comprises determining the amount of radioactivity incorporated into the captured complex. This can be performed by "counting" the samples in a scintillation counter or, in the case where the immobilizing surface is microtiter plate wells, the reacted microtiter plates can be placed in a gamma counter adapted for reading microtiter plates, such as a Packard MATRIX 96, or they can be placed in contact with X-ray film. Where a microtiter plate has been placed in contact with X-ray film, a positive result is observed as a black or exposed area on the X-ray film after it is developed. In such a case the presence of a black region indicates the presence of RSP in the captured complex.

Where the label is a colored bead, the assay mixture is observed to determine if there is "color" adhering to the immobilizing surface. The presence of color indicates the presence of RSP in the captured complex.

Where the label is a fluorescing bead, the presence of fluorescence when exposed to the appropriate excitation wavelength indicates the presence of RSP in the captured complex.

In all the cases described above, the presence of RSP in the captured complex, above a threshold level, indicates the presence of a tumor in the patient from whom the samples were taken.

In a preferred embodiment of the present invention the label is alkaline phosphatase. The enzyme is capable of reacting with synthetic substrates such as 4-methylumbelliferylphosphate (4-MUP) or p-nitrophenyl phosphate (PNPP). The enzyme reacts with 4-MUP to form 4-MU which fluoresces at 460 nm when excited by light at a wavelength of 355 nm. The enzyme reacts with PNPP to form a yellow end product. The presence of fluorescence or yellow color is indicative of a positive reaction for RSP.

Alkaline phosphatase is assayed by adding about 100 µl of solution of about 200 µM 4-MUP, about 100 mM diethanolamine, pH 9.5, about 1 mM $MgCl_2$ and about 0.02% w/v sodium azide, in DPBS, adjusted to a pH of 9.5, to the captured complex. The reaction is incubated at 37° C. for 30 min. The reaction is stopped by the addition of 100 µl of 20 mM EDTA in PBS, adjusted to a pH of 7.2. The fluorescence developed is then quantitated in a FLUOROSKAN fluorescence reader (Labsystems Instruments).

In another preferred embodiment the enzyme is glucose oxidase. Glucose oxidase is assayed in the presence of about 1.5 mg/ml nitro blue tetrazolium (NBT), about 30 mg/ml glucose and about 0.4 mg/ml phenazine methosulfate, an insoluble gray-black product, formazan, is produced. The development of the gray-black color is indicative of a positive reaction, i.e. RSP particles are present in the captured complex.

Quantitative determination is achieved by the intensity of the produced fluorescence or color. The negligible to small RSP production observed with some non-malignant cells is substantially smaller than the RSP production observed with malignant cells and there is little difficulty, using visual colorimetric intensity comparisons, in distinguishing between negligible and significant product formation.

C. Detection of RSP Using "Dip-Stick" Type Assays

In the dip-stick assay an analyte (A) is bound to a surface (S). A labeled binding agent (LBA) is then bound to the analyte. The resultant complex can be represented as follows:

S—A—LBA

In this embodiment of the present invention, about 0.6 µl of serum from a patient is dotted onto a nitrocellulose membrane, or other suitable surface, to which RSP, and other components, in the sample becomes bound. Other binding sites, which remain unreacted on the nitrocellulose, are blocked with FBS, or other suitable blocking material. The membranes are then washed with PBS, adjusted to a pH of 7.2, or other suitable buffer or wash solution, to remove unbound material from the membrane. The washed membranes are contacted with a solution comprising labeled specific binding agent at a concentration of about 1 µg/ml in PBS, adjusted to a pH of 7.2, at about 26° C. for about 15 min. The specific binding agent may be tRNA or anti-RSP antibodies, prepared as described above. The label is also as described above.

In a preferred embodiment the label comprises a two part label. A first part of biotin is attached to the specific binding agent, which is later reacted with a second part of enzyme-streptavidin conjugate. The combination of the two parts forms the label which can then be assayed. When combined the streptavidin, which has a high affinity for biotin, binds to the biotin in a noncovalent reaction that is essentially irreversible. After the combination of the label the membranes are again washed with PBS, adjusted to a pH of 7.2, or other suitable buffer or wash solution, to remove any unbound labeled specific binding agent. The label is then assayed as described above.

In a preferred embodiment the assay is performed by adding about 1.7 µg streptavidin-glucose oxidase in PBS, adjusted to a pH of 7.2, in the presence of about 1.7 µg tRNA-biotin to the RSP bound to the membrane. The membranes are then washed with PBS, adjusted to a pH of 7.2, to remove any unbound tRNA-biotin and streptavidin-glucose oxidase. The dipstick is then immersed in a solution comprising about 1.5 mg/ml nitro blue tetrazolium (NBT), about 30 mg/ml glucose and about 0.4 mg/ml phenazine methosulfate, in a final volume of about 100 µl. The enzymatic oxidation of glucose results in the production of electrons which reduce the nitro blue tetrazolium to formazan. The formazan adheres to the glucose oxidase-streptavidin complex.

Formazan has a blue-black color, therefore, the development of the blue-black color indicates the presence of RSP in the extracellular fluid, which in turn indicates the presence of cancer in the patient from whom the sample was taken. The reaction for assaying of the glucose oxidase can be summarized as follows:

glucose+PM+NBT→formazan+gluconic acid+PM

D. Detection of RSP Using "Competition" Type Assays

One embodiment of a competition type assay involves binding of RSP to a solid surface (S) to form immobilized RSP (S-RSP). An extracellular fluid is then mixed with labeled specific binding agent (LSBA). If RSP is present in the extracellular fluid, LSBA becomes bound to the RSP in the extracellular fluid and is taken "out of solution" so that when the extracellular sample, with the LSBA, is added to the RSP bound to the surface there is no, or little, LSBA available to bind to the S-RSP. This reaction is represented as follows:

S-RSP+RSP sample+LSBA→S-RSP+RSP-LSBA

Therefore, little, or no label is incorporated into the immobilized RSP complex (S-RSP).

On the other hand if there is no RSP present in the extracellular fluid the added LSBA remains "in solution" so that when it is added to the S-RSP it is able to bind, at a maximal level, to the S-RSP. This reaction is represented as follows:

S-RSP+sample+LSBA→S-RSP-LSBA

Therefore, a maximal incorporation into the S-RSP indicates a negative result, i.e. there is no RSP present in the extracellular fluid. Incorporation of lesser amounts of the label in the S-RSP indicate that RSP is present in the extracellular fluid. The amount of RSP in the sample is directly proportional to the reduction in the amount of label present in the S-RSP, when compared to the results of assays conducted with samples in which there is no RSP.

In the case of the competition type assay, S-RSP complexes, and LSBA are prepared as described above.

In another embodiment of the competition type assay, the specific binding agent is immobilized on a surface (S-SBA). An extracellular fluid is then mixed with labeled RSP (LRSP). If RSP is present in the extracellular fluid, the labeled RSP becomes diluted, so that when the mixture is added to the S-SBA both RSP and LRSP become bound. The reaction is summarized as follows:

S-SBA+RSP sample+LRSP→S-SBA-RSP+S-SBA-LRSP

On the other hand if no RSP is present in the extracellular fluid, only LRSP is available to bind to the S-SBA. The reaction is represented by the following:

S-SBA+sample+LRSP→S-SBA-LRSP

Therefore, a maximal incorporation of label into the S-SBA indicates a negative result, i.e. no RSP is present in the extracellular fluid. Incorporation of lesser amounts of the label in the S-SBA indicate that RSP is present in the extracellular fluid. The amount of RSP present in the sample is directly proportional to the reduction of the amount of label present in the S-SBA when compared to the results of assays conducted with samples in which there is no RSP.

In a typical assay, the S-SBA can be antibodies or t-RNA and the label on the LRSP can be an isotope or an enzyme such as alkaline phosphatase.

E. Detection of RSP Using Other Assays Methods

In another embodiment of the present invention RSP are detected using a change in resistance between an anode and a cathode. In this assay, specific binding agent is coated onto both an anode and a cathode, any binding sites remaining are then blocked with RSP-minus serum or other suitable blocking agent. The electrodes are then placed in a suitable electrolytes such as physiological saline, and an appropriate voltage is applied. The resistance is noted. The electrodes are then placed in an extracellular fluid sample, and any RSP present in the sample binds to the specific binding agent. The electrodes are then washed to remove any unbound proteins and re-immersed in the electrolyte solution. A voltage is again applied and the resistance is noted. An increase in the resistance is proportional to the amount of RSP bound to the specific binding agent on the electrode.

In another embodiment of the present invention an agglutination type assay is used. In this reaction colored beads are coated with an RSP specific binding agent (B-SBA). The B-SBA is then mixed with an extracellular fluid sample. If RSP is present in the sample it will bind to the B-SBA. Since the RSP contains multiple binding sites it is able to bind to multiple B-SBA, thus forming an aggregate or "mat." If RSP is not present in the sample, the S-SBA will not form an aggregate. The mixture is then filtered through a membrane which will allow nonaggregated beads to pass through, but which will trap the aggregate. Color on the filter indicates the presence of RSP in the sample.

In another embodiment of the invention, light transmission through the aggregate is measured in a spectrophotometer.

F. Evaluation of Results

The secretion of RSP into extracellular fluids, at high levels, is diagnostic of the presence of cancer in the patient from whom the samples were taken. However, it is important to realize that, with the sensitive assays described above, it is possible to detect very low concentrations of the RSP. Using such tests it has been determined that even in noncancerous conditions, such as benign tumors and atherosclerotic plaques, some RSP is produced which is secreted into the extracellular fluid. The amount of RSP secreted is greatly increased when a tumor is present. The determination of "normal" levels of RSP is required to ensure that a positive result has in fact been obtained. Therefore, it is advisable to include a "control" serum in the assays.

Such a control serum is a serum from a cancer free patient. Also, since conditions such as benign tumors and atherosclerotic plaque increase with age, it is advisable to match the control serum, with respect to age, to the age of the patient. The control establishes the background level, above which results are considered to be positive.

II. Kit for Testing for Cancer

A. Kit for "Sandwich" Type Assays

In one embodiment of the present invention the test for tumors, using the sandwich type assay, is supplied in kit form. Such a kit comprises specific binding agent, labeled specific binding agent, which may be immobilized, and where the label is an enzyme, assay reagents for the enzyme. In using such kits, the user would immobilize the specific binding agent on a surface prior to commencement of the assay. In another embodiment of the invention the kit comprises specific binding agent immobilized on a suitable surface. In addition, the kit may comprise necessary wash and "stop" solutions.

B. Kit for "Dip-Stick" Type Assays

In another embodiment of the present invention the test for tumors, using the dip-stick type assay, is supplied in kit form. Such a kit comprises labeled specific binding agent and, where the label is an enzyme, assay reagents for the enzyme. In using such kits, the user would immobilize extracellular samples on a surface prior to commencement of the assay. In a preferred embodiment, membrane material, as described above, is attached to a support such as a plastic strip. Such strips are included in the kit. In addition, the kit may comprise necessary wash and "stop" solutions.

C. Kit for "Competition" Type Assays

In another embodiment of the present invention the test for tumors, using a competition type assay, is supplied in kit form. Such a kit comprises RSP or specific binding agent, which may be immobilized, labeled specific binding agent, and where the label is an enzyme, assay reagents for the enzyme. In using such kits the user would immobilize the RSP or specific binding agent to a surface prior to commencement of the assay. In another embodiment of the invention the kit comprises RSP or specific binding agent immobilized on a suitable surface. In addition the kit may comprise necessary wash and "stop" solutions.

Example 1

Identification of the Dinucleotide Fold in RSP

An affinity column for the dinucleotide fold in proteins (those enzymes that bind nucleotides as substrates), of AFFIGEL BLUE (100–200 mesh, BioRad Laboratories, Richmond, Calif.) was equilibrated with PBS, adjusted to a pH of 7.2. Culture medium, conditioned by the growth of PC3, human prostate carcinoma cells and known to contain RSP, was loaded on the AFFIGEL BLUE chromatography medium. The medium was then washed with PBS, adjusted to a pH of 7.2, to remove unbound material from the chromatography medium (i.e., proteins without dinucleotide folds). Two ml aliquots of the wash eluate were tested for their protein content, using Coomassie Brilliant Blue G-250 by the method described by Bradford, (Analytical Biochemistry, 72:248, 1976). After all protein species, without dinucleotide folds, were washed from the chromatography medium, the proteins with dinucleotide folds were eluted with 1 mg/ml ($4\times10^{-2}$ mM) tRNA in PBS, adjusted to a pH of 7.2. The tRNA in the buffer results in elution of RSP because the tRNA out competes the AFFIGEL BLUE for the dinucleotide fold binding site on the RSP. The eluted complex consists of RSP-tRNA. The presence of the tRNA in the buffer results in elution of proteins which recognize and bind tRNA, from the chromatography medium.

RSP was found to bind to the chromatography medium indicating that the RSP comprises a dinucleotide fold and that the dinucleotide fold had a specificity for tRNA, since the RSP is eluted in the presence of tRNA.

Example 2

Assaying of RSP with Labeled tRNA

The assay described below relies on the sandwich type assay procedure. The following step-by-step reaction sequence illustrates a reaction where the sample tested contains RSP:
Step 1 tRNA+S[1]→S-tRNA
Step 2 S-tRNA+RSP→S-tRNA-RSP
Step 3 S-tRNA-RSP+tRNA-b[2]→S-tRNA-RSP-tRNA-b
Step 4 S-tRNA-RSP-tRNA-b+SAGO[3]→S-tRNA-RSP-B-tRNA-SAGO
Step 5 S-tRNA-RSP-tRNA-b-SAGO+NBT[4]→gray-black color (formazan)

[1]S=surface
[2]tRNA-b=biotin
SAGO=streptavidin glucose oxidase
NBT=nitro blue tetrazolium In a sample where no RSP is present the reaction sequence is as follows:
Step 1 tRNA+S→S-tRNA
Step 2 S-tRNA+serum→S-tRNA
Step 3 S-tRNA+tRNA-b→S-tRNA
Step 4 S-tRNA+SAGO→S-tRNA
Step 5 S-tRNA+NBT→S-tRNA tRNA was labeled with biotin hydrazide by replacement of the cytidine in tRNA with the hydrazide using sodium bisulfite as a catalyst by incubating 50 µg/ml of tRNA, 10 mg/ml biotin hydrazide, 1M bisulfate, 1M acetate buffer, pH 4.5, in a final volume of 1 ml, at 37° C. for 24 hrs. After the incubation the solution was dialyzed against water at 4° C. for 24 hrs. The dialyzed solution was then dried under vacuum and resuspended in 10 mM Tris-HCl, pH 7.6, 0.1 mM EDTA and stored at 4° C. until required.

The wells of IMMULON microtiter plates, obtained from Dynatech of Chantilly, Va., were coated with streptavidin by contacting the wells of the plates with 100 µl of 20 µg/ml solution of streptavidin in PBS, adjusted to a pH of 7.2. The plates were then incubated at 37° C. for 2 hrs. Any unreacted sites were blocked by incubating the wells for two hours at 37° C. with 300 microliters (µl) of 3% w/v BSA. Biotinylated tRNA was then bound to the streptavidin coated plates.

The coated microtiter wells were filled with 100 µl of medium conditioned by PC3 prostatic carcinoma cells. The medium was concentrated four fold in an Amicon CENTRICON 30 micro-concentrator prior to use. The wells containing the medium were incubated for 60 minutes at 37° C. to bind RSP to the tRNA bound to the microtiter plate wells. At the end of the incubation period the wells were rinsed 10 times with PBS, adjusted to a pH of 7.2.

100 µl of biotin labeled tRNA, prepared as described above, was added to the test wells while 10 µl of 50 mM Tris, pH 7.5, 0.02% w/v sodium azide, without tRNA, was added to negative control wells. The reactions were incubated for 30 minutes at room temperature to bind the biotinylated tRNA to the RSP. The wells were then washed five times with PBS, adjusted to a pH of 7.2, to remove any unbound biotinylated tRNA.

The bound tRNA was then assayed by the addition of 25 µl of 0.1 mg/ml streptavidin-glucose oxidase to all the microtiter wells. The microtiter plates were then incubated for 30 minutes, at room temperature to bind the streptavidin to the biotin on the tRNA. The wells were rinsed 10 times with PBS, adjusted to a pH of 7.2, to remove any unbound streptavidin-glucose oxidase.

Finally, the wells were assayed for glucose oxidase activity by adding 100 µl of 1.5 mg/ml nitro blue tetrazolium, 30 mg/ml glucose and 0.4 mg/ml phenazine methosulfate color reaction mixture to each well. The reactions were incubated at 37° C. and color developed in 45 to 60 min. The reaction, in the test wells, produced formazan which has a strong gray-black color. The negative control wells did not develop any color.

Example 3

Assaying of RSP with Labeled Anti-RSP Antibodies

The assay described below relies on the sandwich type assay procedure. The following step-by-step reaction sequence illustrates a reaction where the sample tested contains RSP:
Step 1 AntiRSPAb[1]+S→S-AntiRSPAb
Step 2 S-AntiRSPAb+RSP→S-AntiRSPAb-RSP
Step 3 S-AntiRSPAb-RSP+AntiRSPAb-AP[2]→S-AntiRSPAb-RSP-AntiRSPAb-AP
Step 4 S-AntiRSPAb-RSP-AntiRSPAb-AP+4MUP[3]→fluorescence

[1]AntiRSPAb =Anti-RSP antibody
[2] AntiRSPAb-AP =Anti-RSP antibody conjugated to alkaline phosphatase
[3]4MUP=4-methylumbelliferylphosphate In a sample where no RSP is present the reaction sequence is as follows:
Step 1 AntiRSPAb+S→S-AntiRSPAb
Step 2 S-AntiRSPAb+serum→S-AntiRSPAb
Step 3 4 S-AntiRSPAb+AntiRSPAb-AP→S-AntiRSPAb
Step 4 S-AntiRSPAb+4MUP→S-AntiRSPAb The wells of IMMULON microtiter plates, obtained from Dynatech of Chantilly, Va., were coated with anti-RSP antibody by contacting the wells of the plates with 100 µl of 20 µg/ml solution of anti-RSP antibody in PBS, adjusted to a pH of 7.2. The plates were then incubated at 37° C. for 2 hrs. Any unreacted sites were blocked by incubating the wells for two hours at 37° C. with 300 microliters (µl) of 3% w/v BSA.

The coated microtiter wells were filled with 100 µl of medium conditioned by PC3 prostatic carcinoma cells. The medium was concentrated four fold in an Amicon CENTRICON 30 micro-concentrator prior to use. The wells containing the medium were incubated for 60 minutes at 37° C. to bind RSP to anti-RSP antibody bound to the microtiter plate wells. At the end of the incubation period the wells were rinsed 10 times with PBS, adjusted to a pH of 7.2.

Anti-RSP antibody was labeled with alkaline phosphatase by mixing 1 mg of antibody with 0.5 of mg alkaline phosphatase suspension, purchased from Sigma Chemical Co. as a 40% suspension in a 65% saturated ammonium sulfate. The mixture was centrifuged at 4,000×g in a microcentrifuge for 6 min. The pellet was resuspended in 1 ml of 0.1M sodium phosphate buffer, pH 6.8. The mixture was dialyzed against three changes of 1,000 ml of 0.1M sodium phosphate buffer, pH 6.8, at 4° C. over a period of at least 24 hrs. The dialysate was then transferred to a 5 ml beaker.

In a fume hood, 2.0 µl of EM grade glutaraldehyde was added to the dialysate and the mixture was stirred slowly for about 5 min. The mixture was then allowed to sit at room temperature for about 17 hrs. After which time about 1 ml of 0.1M ethanolamine, pH 7.0, was added and the mixture was incubated for about 2 hrs. At the end of the incubation the mixture was dialyzed overnight at 4° C. with 3 changes of 1,000 ml of 0.1M sodium phosphate buffer, pH 6.8.

The dialysate was centrifuged in a micro-centrifuge at 4,000×g for 30 min. The resultant pellet was resuspended in 4 ml of 4 mM $ZnCl_2$ and 4 mM $MgCl_2$ and 4 ml of a 100% v/v glycerol was added. The final concentration was 2 mM $ZnCl_2$ and 2 mM $MgCl_2$ in 50% v/v glycerol and the pH of the solution was adjusted to 6.0 and sodium azide was added to a concentration of 0.025% w/v.

The labeled anti-RSP antibody was then placed in the treated wells and incubated for 15 min. at 37° C. to bind the labeled anti-RSP antibody to any RSP in captured complexes in the wells. The wells were washed with PBS, adjusted to a pH of 7.2, to remove any unbound labeled anti-RSP antibody.

Alkaline phosphatase label was assayed by adding 100 μl of solution of 200 μM 4-MUP, 100 mM diethanolamine, pH 9.5, 1 mM MgCl$_2$ and 0.02% w/v sodium azide, in DPBS, adjusted to a pH of 9.5, to the labeled captured complex. The reaction was incubated at 37° C. for 30 min. At the end of the incubation the reaction is stopped by the addition of 100 μl of 20 mM EDTA in PBS, adjusted to a pH of 7.2. The fluorescence developed was quantitated in a FLUOROSKAN fluorescence reader (Labsystems Instruments).

Example 4

Affinity Purification of Anti-RSP Antibodies From Human Serum

Activated cyanogen bromide SEPHAROSE 4-B resin (from Pharmacia) was packed into a column and RSP was bound to the resin by linkage of the NH$_2$ groups of the RSP to the OH groups of the activated cyanogen bromide by passing serum, in which RSP was present, through the chromatography medium. One ml of serum from a former cancer patient was mixed with 3 ml of 0.2M borate buffer, pH 8.5, and was applied to the SEPHAROSE-RSP medium, at room temperature. Any anti-RSP antibody in the serum bound to the RSP on the chromatography medium. Serum proteins, which were not bind to the RSP were washed from the medium with PBS, adjusted to a pH of 7.2, and the absorbance of the material washed from the chromatography medium was monitored at 280 nm ($A_{280}$).

When the $A_{280}$ was reduced to 0, bound anti-RSP antibody were eluted from the chromatography medium by the addition of 2 ml aliquots of 4.0M magnesium chloride. Each of the aliquots were collected separately and the $A_{280}$ of each of the eluates was monitored. The results are summarized in Table I.

TABLE I

| Eluate No. | $A_{280}$ |
|---|---|
| 1 | 0.04 |
| 2 | 0.02 |
| 3 | 0.02 |
| 4 | 0.01 |

The decreasing level of $A_{280}$ values (i.e. protein; anti-RSP antibody) indicated that the anti-RSP antibody was eluted in the first four fractions. These four fractions were pooled and dialyzed against 0.85% w/v sodium chloride at 4° C. for 18 hours, then for 2.5 hours against PBS, adjusted to a pH of 7.2, to remove the excess salt.

The dialysate was centrifuged at 1,500×g for 15 min. to remove any particulate matter that may have formed during dialysis. The resultant 15 ml supernatant was concentrated to 2.5 ml in an Amicon Ultrafiltration cell with a PM-10 membrane.

The final concentration of the affinity purified anti-RSP antibody was determined to be 0.1 mg/ml.

Example 5

Assay of RSP with Anti-RSP Antibody

Anti-RSP antibody, prepared in accordance with the method described in Example 4, was applied to a nitrocellulose membrane attached to a plastic stick with double sided SCOTCH tape. Any unbound sites on the nitrocellulose were blocked by dipping the membrane into normal serum. The dip-sticks were then exposed to 0.1 ml of serum from a cancer patient for 10 minutes at room temperature. At the end of the incubation the membrane was washed with distilled water, blotted dry and exposed to labeled tRNA, prepared in accordance with the method described in Example 2, for 15 minutes. The step-wise reactions are illustrated as follows:

Step 1 Ab[1]+M[2]→M-Ab
Step 2 M-Ab+RSP→M-Ab-RSP
Step 3 M-Ab-RSP+tRNA-b[3]→M-Ab-RSP-tRNA-b
Step 4 M-Ab-RSP-tRNA-b+SAGO[4]→M-Ab-RSP-tRNA-b-SAGO
Step 5 M-Ab-RSP-tRNA-b-SAGO+NBT[5]→black, insoluble product (Formazan)

[1]Ab=polyclonal anti-RSP antibody
[2]M=membrane
[3]tRNA-b=tRNA-biotin
[4]SAGO=streptavidin glucose oxidase
[5]NBT=nitro blue tetrazolium The reactions resulted in the characteristic formazan gray-black spot only where the anti-RSP antibody had been applied to the membrane.

This example illustrates that the RSP was captured out of the cancer serum by the anti-RSP antibody affixed on the membrane.

Example 6

Purification of RSP from Serum

Proteins, including RSP, were precipitated from 300 ml serum obtained from a breast cancer patient, by bringing the serum to 50% saturation with ammonium sulfate. The precipitate was collected by centrifugation at 1,500×g for 20 min. at room temperature and then dissolved in TDG buffer (50 mM Tris-HCl, pH 7.5, 1 mM dithiothreitol, 20% v/v glycerol and 0.02% w/v sodium azide). The proteins were reprecipitated by bringing the solution to 50% saturation with ammonium sulfate. The precipitate was collected by centrifugation at 1,500×g for 20 min. at room temperature and was then redissolved in TDG buffer. The precipitation of the proteins was repeated once more and the precipitate was redissolved in TDG buffer and dialyzed, in a 10,000 molecular weight cut-off dialysis membrane, against PBS, adjusted to a pH of 7.2, with 0.02% sodium azide, at 4° C. for 18 hours.

The dialysate (10 ml) was then applied to BIOGEL A-0.5 m resin packed in a 4×8 cm column. The resin was equilibrated with TDG buffer prior to use. After the dialysate was applied to the BIOGEL A-0.5 m resin, it was washed with TDG buffer and fractions were collected. The fractions were tested for the presence of RSP in accordance with the method described in Example 5.

The RSP containing fractions were pooled and dialyzed against PDG buffer (25 mM potassium phosphate, pH 6.8, 1 mM dithiothreitol and 20% (v/v) glycerol) for 18 hours at 4° C. The dialysate was then concentrated and applied to 25 ml of hydroxylapatite packed into a column and equilibrated with PDG buffer. The hydroxyapatite was washed with PDG buffer to removed unbound material. RSP was eluted from the hydroxylapatite with a 100 ml linear salt gradient from 100 to 150 mM potassium phosphate, pH 6.8, in 1 mM dithiothreitol and 20% (v/v) glycerol. Fractions were collected and tested for the presence of RSP in accordance with the method described in Example 5.

The RSP-containing fractions were pooled and dialyzed against TDG buffer for 18 hours at 4° C. The dialysate was then applied to 20 ml AFFIGEL BLUE packed into a column and equilibrated with the TDG buffer. The column was washed with 50 ml of TDG buffer after which the RSP were eluted with 100–130 ml of a gradient from 0 to about 0.6M potassium chloride, in TDG buffer. The fractions containing RSP, assayed in accordance with the methods described in Example 5, were pooled and dialyzed against TDG buffer for 18 hours at 4° C. The dialysate was concentrated, with centrifugation at 1,500×g, in a Amicon cell with a PM-10 membrane, to a final protein concentration of 5 mg/ml, estimated by the $A_{280}$ of the sample.

The purity of the RSP was determined by polyacrylamide gel electrophoresis. The gels indicated that the sample contained a single band with a molecular weight of about 600,000 to about 75,000.

Example 7

Preparation of Anti-RSP Antibodies

Primary immunization was performed by injecting a rabbit with 100 μg of RSP, prepared in accordance with the method described in Example 6, in an equal volume of complete Freund's adjuvant, at multiple subcutaneous sites. After a three-week interval a secondary immunization was performed by injecting 50 μg of RSP, in an equal volume of incomplete Freund's adjuvant, at multiple subcutaneous sites.

Nine to ten days after the secondary injection the rabbit was bled to determine the anti-RSP antibody titer of the serum.

After an additional fourteen-to-eighteen-day interval a third immunization was performed by injecting 50 μg RSP in an equal volume of incomplete Freund's adjuvant subcutaneously at multiple sites. After a nine-to-eleven-day interval the rabbits were bled for the production of anti-RSP antibody.

Immunoglobulins were separated from the serum by passing the serum over a Protein G-agarose packed into a column, to remove IgM, then through human serum protein agarose packed into a column, to remove any nonspecific anti-human antibodies, then through RSP Sepharose, prepared in accordance with the method described in Example 4, which was also packed into a column. The anti-RSP antibodies were eluted from the RSP Sepharose with 0.2 M acetic acid. Fractions were neutralized by collecting the eluate in tubes containing 100 μl of 50 mM Tris, pH 7.5, containing 0.1M NaCl. Fractions with an $A_{280}$ greater than 0.01 were pooled and concentrated in an Amicon cell with a PM-10 membrane, as described above, to a concentration of about 1 mg/ml.

The anti-RSP antibody preparation was preserved with 0.02% w/v sodium azide and stored at 5° C.

Example 8

Assay of RSP with tRNA

A 0.6 μl sample of human serum was dotted onto a dipstick, comprising 3×5 millimeters (mm) nitrocellulose membrane attached to a 3×40 mm plastic strip. Any unbound sites on the nitrocellulose were blocked with normal human serum. The nitrocellulose was then washed and hydrated in distilled water and blotted dry. The sample was then assayed to detect any RSP present in the sample and is summarized as follows:

Step 1 $M^1$-RSP+tRNA-$b^2$→M-RSP-tRNA-b
Step 2 M-RSP-tRNA-b+SAGO$^3$→M-RSP-tRNA-b-SAGO
Step 3 M-RSP-tRNA-b-SAGO+NBT→insoluble grey-black color (Formazan)

[1]M=membrane
[2]tRNA-b=biotinylated tRNA
[3]SAGO=streptavidin glucose oxidase
[6]NBT=nitro blue tetrazolium The sample was then dipped in a solution containing biotinylated-tRNA (1 mg/ml), prepared in accordance with the method described in Example 2, to bind the tRNA to any RSP present in the serum sample. The tRNA bound sample was then reacted with glucose oxidase labeled streptavidin (1 mg/ml) by the method described in Example 2. The glucose oxidase-streptavidin was purchased from Sigma Chemical Co. The streptavidin binds to biotin on the tRNA, thus labeling the complex with glucose oxidase. The result is then visualized by the addition of glucose and nitro blue tetrazolium. The action of the glucose oxidase on glucose results in the generation of electrons which reduce the tetrazolium to formazan particles. The formazan particles, which have an intense gray-black color, adhere to the glucose oxidase thus indicating a positive reaction by the gray-black spot which develops on the membrane at the site where the serum sample was placed.

In a blind study, the assay correctly identified 71/73 sera as being from cancer patients, 53/62 as being from noncancer patients or patients in remission and 38/45 as from patients with non-malignant conditions. The results are presented in Tables II, III and IV.

TABLE II

| PATIENT TESTED WITH A MALIGNANCY AS INDICATED | NO. TESTED | NO. POSITIVE |
| --- | --- | --- |
| Adenocarcinoma | 2 | 0 |
| Bladder Cancer | 1 | 1 |
| Brain Tumor | 2 | 2 |
| Breast Cancer | 16 | 16 |
| Cervical Carcinoma | 1 | 1 |
| Colon Cancer | 4 | 4 |
| Eye | 1 | 1 |
| Head and Neck | 1 | 1 |
| Leukemia | 7 | 7 |
| Lung Ca | 8 | 8 |
| Lymphoma | 11 | 11 |
| Malignant Melanoma | 3 | 3 |
| Metastatic Carcinoma | 2 | 2 |
| Multiple Myeloma | 3 | 3 |
| Nasal Carcinoma | 1 | 1 |
| Ovarian Cancer | 5 | 5 |
| Pancreatic Cancer | 1 | 1 |
| Squamous Cell Cancer | 1 | 1 |
| Testicular Cancer | 1 | 1 |
| Thyroid Cancer | 2 | 2 |
| Total Tested/Positive Sensitivity = 97.2% (71/73 × 100) | 73 | 71 |

TABLE III

| PATIENT TESTED WITH A TUMOR, AS INDICATED, IN REMISSION | NO. TESTED | NO. POSITIVE |
| --- | --- | --- |
| Adenocarcinoma | 1 | 0 |
| Adrenal Cell Carcinoma | 1 | 1 |
| Breast Cancer | 8 | 1 |
| Hodgkins Disease | 1 | 0 |
| Leukemia | 1 | 0 |
| Lymphoma | 2 | 0 |
| Prostatic Cancer | 1 | 0 |
| Total Tested/Positive Sensitivity = 86.6% (13/15 × 100) | 15 | 2 |

TABLE IV

| PATIENT TESTED, WITH A NON-MALIGNANT CONDITION AS INDICATED | NO. TESTED | NO. POSITIVE |
| --- | --- | --- |
| Anemia | 7 | 0 |
| Benign Liver Mass | 1 | 1 |

TABLE IV-continued

| PATIENT TESTED, WITH A NON-MALIGNANT CONDITION AS INDICATED | NO. TESTED | NO. POSITIVE |
|---|---|---|
| Bleeding Dyscrasia | 2 | 0 |
| Bronchitis | 1 | 0 |
| Carcinoid Syndrome | 1 | 0 |
| Cervical Myelopathy | 1 | 0 |
| Cirrhosis | 1 | 0 |
| Costovertebral Angle | 1 | 0 |
| Embolus | 1 | 0 |
| Gastrointestinal Bleeding | 1 | 0 |
| Guillain-Barre Syndrome | 1 | 0 |
| Hypertension | 1 | 0 |
| Hyperthyroidism | 1 | 0 |
| Leucocytosis | 1 | 0 |
| Lupus | 4 | 4 |
| Lymphocytosis | 1 | 1 |
| Monoclonal Gammopathy | 1 | 0 |
| Multiple Sclerosis | 1 | 1 |
| Myeloid Metaplasia | 1 | 0 |
| Myeloproliferative Disease | 1 | 0 |
| Neutropenia | 1 | 0 |
| Normal (no disease) | 6 | 0 |
| Pelvic Inflammation | 1 | 0 |
| Peptic Ulcer | 1 | 0 |
| Periarteritis | 1 | 0 |
| Pneumonia | 1 | 0 |
| Polycythemia | 1 | 0 |
| Sepsis | 1 | 0 |
| Thrombophlebitis | 1 | 0 |
| Thrombosis | 1 | 0 |
| Total Tested/Positive | 45 | 7 |

Sensitivity = 84.4% (38/45 x

Example 9

Detection of RSP Antibody Using Anti-RSP Polyclonal Antibodies

Affinity purified polyclonal anti-RSP antibodies, prepared in accordance with the method described in Example 4, were immobilized on the surface of 1 μm diameter protein coated latex beads purchased from Polyscience. The anti-RSP antibodies were immobilized by mixing 650 ml of anti-RSP antibodies with 650 μl of bead suspension. The mixture was incubated for 2.5 hrs at 37° C. The beads were washed once with PBS, adjusted to a pH of 7.2, resuspended in 650 μl of PBS, adjusted to a pH of 7.2, and unreacted sites were blocked by incubating the beads with an equal volume (650 μl) of normal human plasma for 1 hr. at 37° C. The beads were washed once with PBS then resuspended in 1 ml PBS, adjusted to a pH of 7.2, to which was added 0.05% w/v sodium azide.

65 μl of the anti-RSP antibody coated beads were mixed with 40 μl of patient serum and the mixture incubated for 15 min. At the end of the incubation aliquots of the mixture were transferred to glass fiber membranes resting on a column of absorbent material. The beads remained on the membrane surface and the fluid component was absorbed by the absorbent material. The beads were washed with PBS, adjusted to a pH of 7.2, and mixed with 70 μl of antibody, labeled with alkaline phosphatase, prepared in accordance with Example 3. The mixture was incubated at 37° C. for 15 min. then washed with 50 mM Tris, pH 7.5, 20% v/v glycerol, 3% w/v goat serum. The membrane was then contacted with 68 μl of 200 μM 4-MUP, 100 mM diethanolamine, pH 9.5, 1 mM $MgCl_2$ and 0.02% w/v sodium azide, in DPBS, adjusted to a pH of 9.5. The samples were excited with light at a wavelength of 355 nm and the resultant fluorescence emitted at 460 nm wavelength was read and recorded. The amount of RSP in the sample was then extrapolated from a standard curve developed from serum "spiked" with RSP at 0, 4, 10, 60, 100 and 200 μg/ml. The assays were performed in a commercially available "IMX" testing device, manufactured by Abbott Laboratories.

Testing of over 60 noncancer patients with this system set the cut off for normal RSP levels at 16 μg/ml. This value is 2 standard deviations above the mean for the normal RSP serum levels.

Example 10

Evaluation of Patients with Various Pulmonary Diseases for Serum RSP Levels

In a blind study, which included 46 patients with active lung cancer and 80 noncancerous controls that included 35 normal patients, 24 smokers, and 21 patients with chronic obstructive pulmonary disease (COPD) for a total of 126 patients, patients were assayed for serum RSP levels by the method described in Example 9. The RSP tumor marker was able to correctly identify over 93.3% of the active lung cancer patients as positive for cancer, 100% of the normals as negative for cancer, 95.8% of the smokers as negative for cancer, and 95.0% of the patients with COPD as negative for cancer. Results are presented in Table V.

TABLE V

RSP Response in Patients with Lung Cancer

| Category | No. Tested | No. Correct | % Correct |
|---|---|---|---|
| Normals | 35 | 35 | 100 |
| Smokers | 24 | 23 | 95 |
| COPD[1] | 21 | 19 | 90.5[2] |
| Lung Cancer | 46 | 42 | 91.3[3] |

[1]COPD = chronic obstructive pulmonary disease
[2]One of the false positives developed lung cancer 8 months later. The corrected % correct was 95%
[3]One false negative was in complete remission when tested. The corrected % correct was 93.3%

Example 11

Evaluation of Patients with Breast Cancer for Serum RSP Levels

In a blind study, which included 42 patients with active breast cancer, 120 patients with breast cancer in remission for greater than five years, and 61 normal controls that totaled 223 patients, patients were assayed for serum RSP levels by the method described in Example 9. The patients were tested with the RSP tumor marker, CEA, and CA15-3. The RSP tumor marker correctly identified 92.8% of the cancers, CEA identified 30.9%, and CA15-3 correctly identified 72.2%. The results are presented in Table VI.

TABLE VI

RSP, CEA and CA15-3 Comparisons Between Normals, and Active Breast Cancer and Inactive Breast Cancer patients

| Patient Category | Tumor Marker | Total Tested | Total Correct | % Accuracy |
|---|---|---|---|---|
| Normal | RSP | 61 | 60 | 98.4 |
|  | CEA | 59 | 57 | 96.6 |
|  | CA15-3 | 52 | 51 | 98.1 |
| Active | RSP | 42 | 39 | 92.8 |

TABLE VI-continued

RSP, CEA and CA15-3 Comparisons Between Normals, and Active Breast Cancer and Inactive Breast Cancer patients

| Patient Category | Tumor Marker | Total Tested | Total Correct | % Accuracy |
|---|---|---|---|---|
| | CEA | 42 | 13 | 30.9 |
| | CA15-3 | 36 | 26 | 72.2 |
| Remission ≧ 5 years | RSP | 120 | 110 | 91.7 |
| | CEA | 119 | 115 | 96.6 |
| | CA15-3 | 101 | 92 | 91.1 |
| Remission ≦ 5 years | RSP | 145 | 112 | 84.1 |
| | CEA | 87 | 82 | 94.3 |
| | CA15-3 | 70 | 61 | 87.1 |

RSP Serum Concentration > 15 µg/ml = positive test for cancer
CEA Serum Concentration > 6 ng/ml = positive test for cancer
CA15-3 Serum concentration > 30 units/ml = positive test for cancer

Example 12

Evaluation of Patients with Ovarian Cancer for Serum RSP Levels

In a third blind study, which included 11 patients with stage III disease, patients were assayed for serum RSP levels. The RSP test correctly identified 10 out of 10 patients that were active-positive and one as negative that was in complete remission. The results are presented in Table VII.

TABLE VII

RSP Response in Patients with Ovarian Cancer

| Total | Positives | Negatives | Sensitivity |
|---|---|---|---|
| 11 | 10 | 1* | 90.9% |

*The patient was in complete remission when tested. Therefore, the corrected sensitivity was 100%

Example 13

Evaluation of Patients Undergoing Curative Treatment for Cancer

Figure 3:
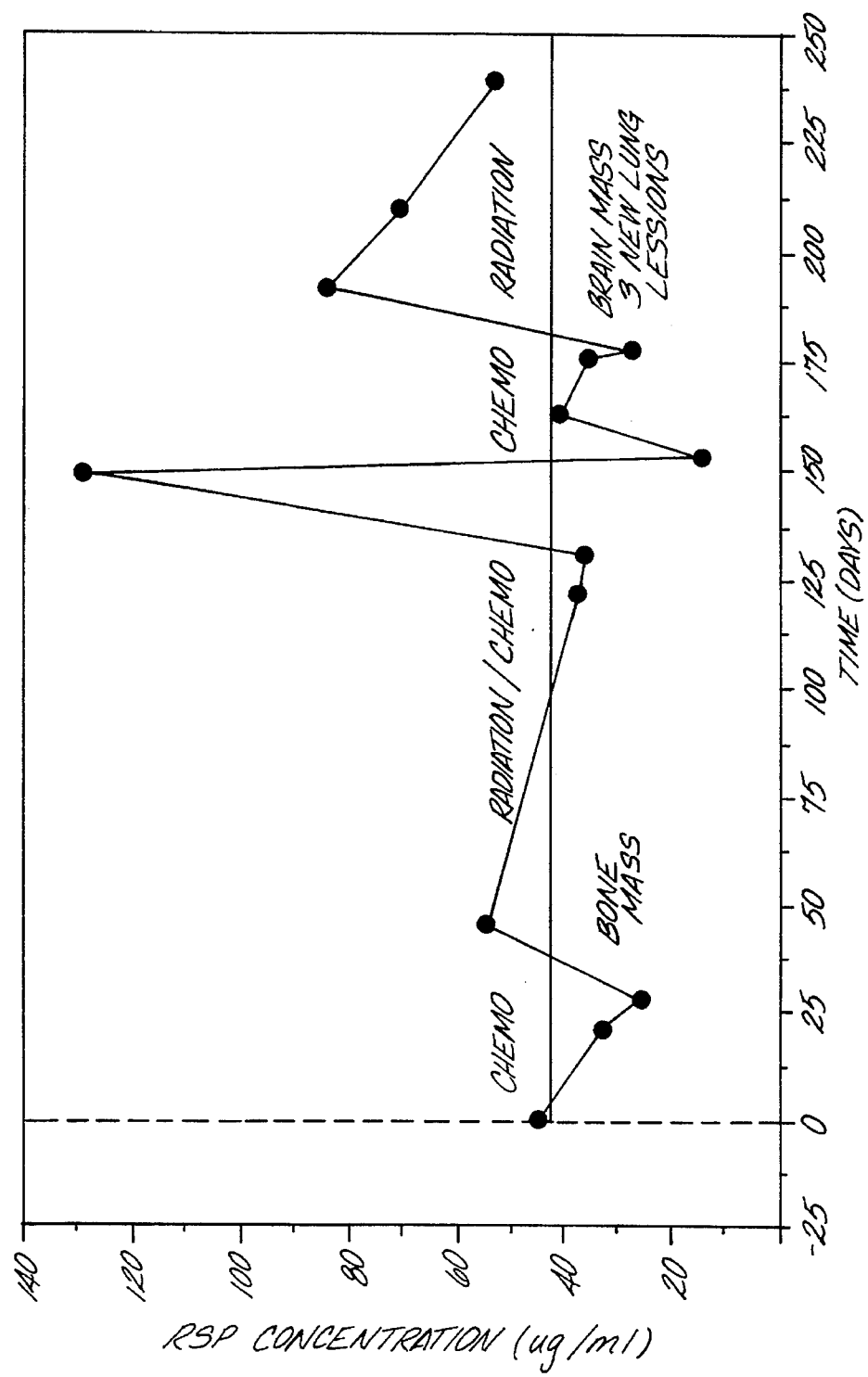
FIG. 3 illustrates a plot of RSP concentration vs. time in a study following the progress of a lung cancer patient undergoing curative treatment.
Figure 4:
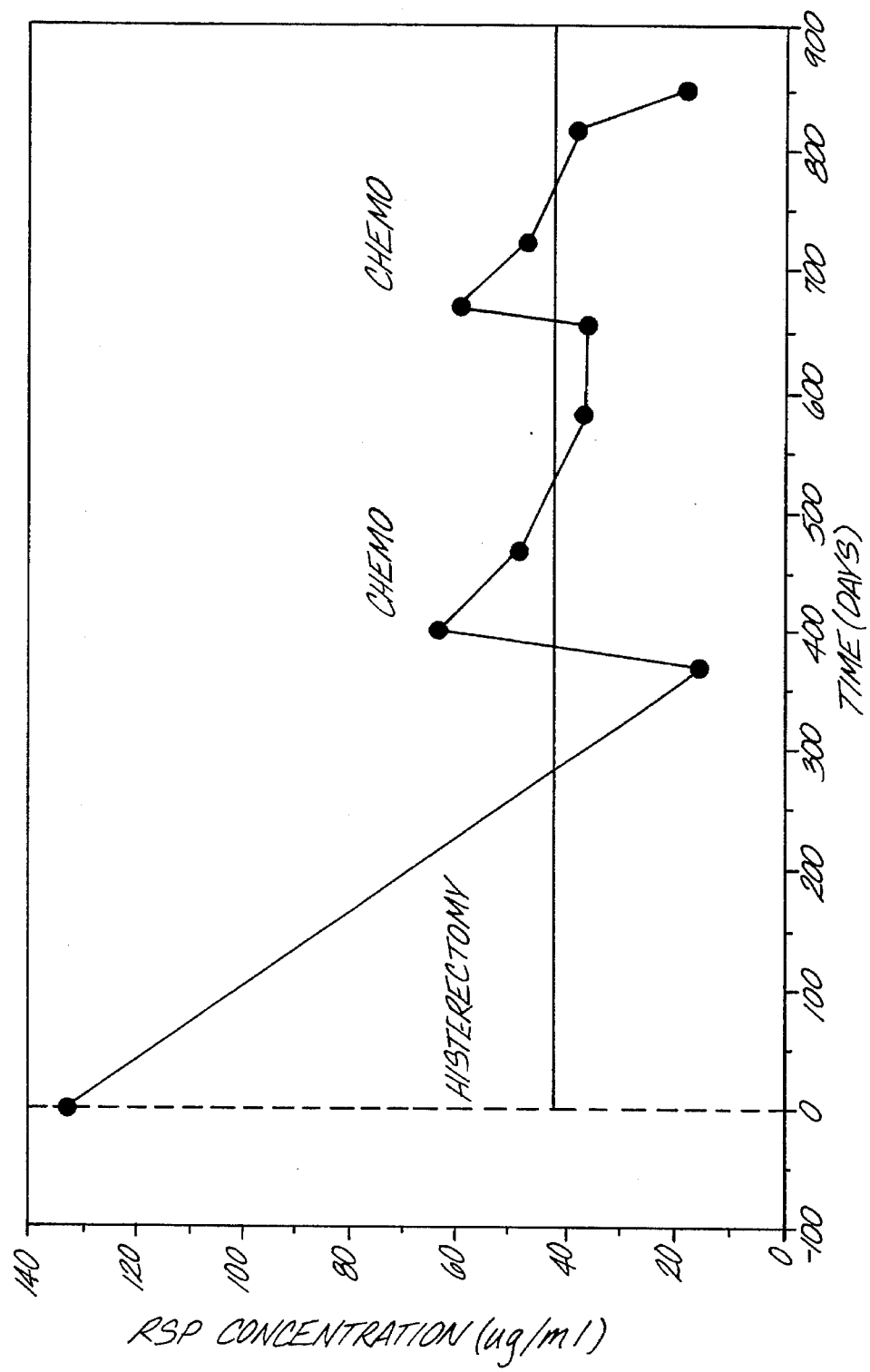
FIG. 4 illustrates a plot of RSP concentration vs. time in a study following the progress of an ovarian cancer patient undergoing curative treatment.

The test system has also been used to track patients over time while undergoing curative treatment for cancer. The test system correctly tracked the pathological observations in 11 of 13 lung cancer patients and in 3 of 3 ovarian cancer patients. Representative examples are illustrated in FIGS. 3 and 4.

Example 14

Detection of RSP with a Competitive Inhibition Assay

In this assay 100 µl of a 20 µg/ml solution of RSP was immobilized on the floor and walls of microtiter wells from Dynatech. The wells were blocked with 3% w/v BSA diluted in PBS, adjusted to a pH of 7.4. To demonstrate the reproducibility of the competitive inhibition test system for measuring RSP in a protein solution, purified RSP was diluted in DPBS, adjusted to a pH of 7.4, containing 3% w/v BSA to give 5, 10, 20, 30, 40, 50 or 60 µg/ml RSP. Ten µl of each of the RSP dilutions and 90 µl of affinity purified anti-RSP antibody, conjugated with alkaline phosphatase, prepared in accordance with method of Example 3, were dispensed into duplicate wells. The plate was sealed and incubated for 1 hr. at 37° C., with gentle rocking.

Unbound conjugate was removed by washing the wells twice with PBS, adjusted to a pH of 7.4. Then 100 µl of a solution of 200 µM 4-MUP, 100 mM diethanolamine, pH 9.5, 1 mM $MgCl_2$ and 0.02% w/v sodium azide, in DPBS, adjusted to a pH of 9.5, was added to each well. After 6 min. incubation 50 µl of 20 mM EDTA was added to stop the reaction. The fluorescence of each well was excited with a light source at 355 nm with a FLUOROSKAN fluorescence reader (Labsystems Instruments). The results, which show a negative linear slope, when plotted, as is appropriate with a competitive reaction based assay, is presented in Table VIII. The slope has a correlation of 0.991.

TABLE VIII

Dose Response Generated with a Competitive Inhibition Assay

| RSP (µg/ml) | Fluorescence Values in Duplicate | | Mean | Standard Deviation | % CV[1] |
|---|---|---|---|---|---|
| 5 | 3556 | 3130 | 3343 | 302 | 9.0 |
| 10 | 3282 | 3080 | 3183 | 140 | 4.4 |
| 20 | 2311 | 2684 | 2947 | 373 | 12.6 |
| 30 | 2707 | 2309 | 2508 | 281 | 11.2 |
| 40 | 1911 | 2172 | 2042 | 185 | 9.0 |
| 50 | 1657 | 1741 | 1699 | 59 | 3.5 |
| 60 | 1380 | 1577 | 1479 | 139 | 9.4 |

[1]%CV = Coefficient of variation = standard deviation/mean × 100

Example 15

Detection of RSP Using $^{125}$I-tRNA

IMMULON 2 strip wells from Dynatech were coated with anti-RSP antibodies and were blocked with 3% w/v BSA in PBS, adjusted to a pH of 7.4. The wells were washed twice with PBS, adjusted to a pH of 7.4, then 50 µl of a 1:100 dilution of a 5.7 mCi solution of $^{125}$I-tRNA (prepared by New England Nuclear, of Boston Mass., under contract) and 50 µl of test sera were added to each well. The test sera included serum from 5 normal, healthy individuals and 5 patients with active breast cancer.

Each serum sample was assayed in triplicate. The sera were incubated for 2 hr at room temperature during which time the radio-labeled tRNA became bound to the dinucleotide folds in the RSP molecules and concurrently, the immobilized anti-RSP captured the RSP-$^{125}$-tRNA complex out of the sera onto the solid surface of the wells.

The sera was removed by aspiration and the wells were washed 4 times with PBS, adjusted to a pH of 7.4. The individual wells were placed in 12×75 mm glass counting tubes and the average counts per min. (cpm), minus background, was determined in a gamma counter. The results are summarized in Table IX.

TABLE IX

Average cpm for Cancer Patients and Normal Patients

| Breast Cancer Patients | | Normal Patients | |
|---|---|---|---|
| Patient | Average cpm | Patient | Average cpm |
| 1 | 35 | 1 | 18 |
| 2 | 34 | 2 | 11 |
| 3 | 37 | 3 | 21 |
| 4 | 30 | 4 | 9 |
| 5 | 26 | 5 | 18 |

Example 16

Detection of RSP Using $^{125}$I-tRNA tRNA was immobilized on the surface of IMMULON microtiter wells. Fifty µl of serum from five cancer patients and five noncancer patients were each placed in separate wells for a total of 30 separate wells, i.e., each of the serums were assayed in triplicate. The serum samples were incubated in the tRNA coated wells for 2 hr at room temperature. At the end of the incubation the wells were washed with PBS, adjusted to a pH of 7.2, and 150 μl of $^{125}$I-tRNA was added. The microtiter plates were incubated for 7 hr at room temperature. At the end of the incubation the wells were washed five times with PBS, adjusted to a pH of 7.2, and then counted in a gamma counter. The results obtained (cpm) from the triplicate samples were added together and divided by three, to give the average cpm for each patient tested. The results are summarized in Table X.

TABLE X

| Normal Patients | | Cancer Patients | | |
| --- | --- | --- | --- | --- |
| Patient No. | Average cpm | Patient No | Cancer Type | Average cpm |
| 1 | 83 | 1 | Lung | 205 |
| 2 | 119 | 2 | Lung | 166 |
| 3 | 101 | 3 | Prostate | 166 |
| 4 | 103 | 4 | Breast | 67 |
| 5 | 88 | 5 | Colon | 142 |

From the results it can be seen that, assuming a value of about 130 above which the cpm obtained indicate the presence of cancer and below which the cpm indicate the absence of cancer, all negatives and four out of five positives were correctly diagnosed.

The above description of preferred embodiments of the for the detection of RSP and methods associated with the use of the detection of RSP is for illustrative purposes. Variations will be apparent to those skilled in the art. For example, RSP can also be found in almost all living organisms, therefore, the detection of RSP in the extracellular fluids of organisms other than humans, such as commercial animals, would also be indicative of cancer. Therefore, the present invention is not intended to be limited to the particular embodiments described above. In addition the invention can be practiced in the absence of any element not specifically disclosed. The scope of the invention is defined in the following claims.

What is claimed:

1. A method for identifying the presence of tumors in a human patient comprising:

immobilizing ringed shaped particles (RSP) from an extracellular fluid sample on a solid surface, wherein the solid surface is coated with an RSP binding agent selected from the group consisting of tRNA molecules and anti-RSP antibodies; and assaying for RSP immobilized on the surface with a labeled binding agent selected from the group consisting of tRNA, labelled peptides and anti-RSP antibodies, wherein the amount of RSP, two standard deviations above the mean of the values obtained with normal patients is indicative of the presence of cancer.

2. A method as recited in claim 1 wherein the RSP specific binding agent is immobilized on a surface selected from the group consisting of wells of microtiter plates, glass slides, beads and nitrocellulose membranes.

3. A method as recited in claim 1 wherein the label is selected from the group consisting of a radioactive agent, an enzyme, a dye, a bioluminescent agent, a chemiluminescent agent and colored beads.

4. A method for identifying the presence of tumors in a human patient comprising:

immobilizing RSP specific binding agent on a surface, wherein the specific binding agent is selected from the group consisting of tRNA and anti-RSP antibodies;

contacting a sample of extracellular fluid from a patient to the immobilized RSP specific binding agent to form a captured complex;

contacting the captured complex with a labeled specific binding agent to form a labeled captured complex; and quantitating the amount of RSP in the captured complex, wherein the amount of RSP, two standard deviations above the mean of the values obtained with normal patients is indicative of the presence of cancer.

5. A method as recited in claim 4 wherein the RSP specific binding agent is immobilized on a surface selected from the group consisting of wells of microtiter plates, glass slides, beads and nitrocellulose membranes.

6. A method as recited in claim 4 wherein the labeled RSP specific binding agent is selected from the group consisting of labeled tRNA, labeled anti-RSP antibodies and labeled peptides.

7. A method as recited in claim 4 wherein the label is selected from the group consisting of a radioactive agent, an enzyme, a dye, a bioluminescent agent, a chemiluminescent agent and colored beads.

\* \* \* \* \*

UNITED STATES PATENT AND TRADEMARK OFFICE
CERTIFICATE OF CORRECTION

PATENT NO. : 5,459,035                   Page 1 of 2

DATED : October 17, 1995

INVENTOR(S) : Guerrero et al.

It is certified that error appears in the above-identified patent and that said Letters Patent is hereby corrected as shown below:

On title page, item

[63], line 1, "Aug. 20, 1991," should read --Aug. 30, 1991,--"

[63], line 4, "Dec. 5, 1988," should read --Dec. 15, 1988,--"

[63], line 5, "Jul. 12, 1990," should read --Jul. 13, 1990,--"

In column 1, line 10, "Aug. 20, 1991," should read --Aug. 30, 1991,--

In column 1, line 12, "Jul. 12, 1990," should read --Jul. 13, 1990,--

In column 1, line 16, "Dec. 5, 1988," should read --Dec. 15, 1988,--

In column 2, line 35, "agent," should read --agent--

In column 2, line 41, "agent," should read --agent--

In column 2, line 51, "of-" should read --of--

In column 4, line 48, "Briefly," --starts a new paragraph--

In column 6, line 5, delete "," after "(hybridomas)," should read --(hybridomas)--

In column 7, line 61, "contracted" should read --contacted--

In column 13, line 9, "t-RNA" should read --tRNA--

In column 13, line 19, "electrolytes" should read --electrolyte--

In column 14, lines 47, 48, delete "," after Biochemistry should read --Biochemistry--

In column 15, line 39, "four fold" should read --four-fold--

UNITED STATES PATENT AND TRADEMARK OFFICE
CERTIFICATE OF CORRECTION

PATENT NO. : 5,459,035

DATED : October 17, 1995

INVENTOR(S) : Guerrero et al.

It is certified that error appears in the above-identified patent and that said Letters Patent is hereby corrected as shown below:

In column 16, line 31, "four fold" should read --four-fold--

In column 17, line 23, "bound" should read --binds--

In column 18, line 47, "RSP containing" should read "RSP-containing"

In column 20, line 16, "non-malignant" should read --nonmalignant--

In column 21, line 31, "(38/45 x" should read --(38/45 x 100)--

In column 24, line 67, "placed in separate" should read --placed in three separate--

In column 25, line 29, "of the" should read --of the processes--

Signed and Sealed this

Twenty-fifth Day of June, 1996

Attest:

BRUCE LEHMAN

*Attesting Officer*  *Commissioner of Patents and Trademarks*